United States Patent
True et al.

(10) Patent No.: US 12,336,769 B2
(45) Date of Patent: Jun. 24, 2025

(54) MAGNETIC FIELD SENSOR FOR A MEDICAL DEVICE

(71) Applicant: Boston Scientific Scimed Inc., Maple Grove, MN (US)

(72) Inventors: Kyle P. True, Minneapolis, MN (US); David A. Chizek, Brooklyn Park, MN (US); Daniel J. Foster, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 286 days.

(21) Appl. No.: 17/747,269

(22) Filed: May 18, 2022

(65) Prior Publication Data
US 2022/0370149 A1 Nov. 24, 2022

Related U.S. Application Data

(60) Provisional application No. 63/190,537, filed on May 19, 2021.

(51) Int. Cl.
*A61B 34/20* (2016.01)
*G01R 33/032* (2006.01)

(52) U.S. Cl.
CPC ............ *A61B 34/20* (2016.02); *G01R 33/032* (2013.01); *A61B 2034/2051* (2016.02); *A61B 2034/2072* (2016.02)

(58) Field of Classification Search
CPC ............ A61B 34/20; A61B 2034/2051; A61B 2034/2072; A61B 5/6847; A61B 5/6886; A61B 5/7228; A61B 5/06; G01R 33/032
See application file for complete search history.

(56) References Cited

U.S. PATENT DOCUMENTS

| | | |
|---|---|---|
| 4,543,954 A | 10/1985 | Cook et al. |
| 5,644,230 A | 7/1997 | Pant et al. |

(Continued)

FOREIGN PATENT DOCUMENTS

| | | |
|---|---|---|
| EP | 3139189 A1 | 3/2017 |
| EP | 3363359 A1 | 8/2018 |
| WO | 2016/171597 A1 | 10/2016 |

OTHER PUBLICATIONS

International Search Report and Written Opinion issued in PCT/US2019/013651, mailed May 2, 2019, 12 pages.

(Continued)

*Primary Examiner* — Akm Zakaria
(74) *Attorney, Agent, or Firm* — Nelson Mullins Riley & Scarborough LLP

(57) ABSTRACT

A magnetic field sensor for a medical device, the magnetic sensor assembly comprising a substrate having a plurality of planar sections, wherein adjacent planar sections are joined by a transition section, and wherein the planar sections are arranged in a substantially C-shaped arrangement such that an inner surface of the magnetic field sensor is concave, and wherein the plurality of planar sections includes a first planar section oriented in a first plane and a second planar section oriented in a second plane orthogonal to the first plane. A first magneto-resistive (MR) sensor is mounted to the first planar section and defining a first axis of sensitivity, and a second MR sensor is mounted to the second planar section and defining a second axis of sensitivity that is orthogonal to the first axis of sensitivity.

16 Claims, 6 Drawing Sheets

(56) References Cited

U.S. PATENT DOCUMENTS

| | | | |
|---|---|---|---|
| 6,169,254 B1 | 1/2001 | Pant et al. | |
| 6,184,680 B1 | 2/2001 | Shinoura et al. | |
| 6,536,123 B2 | 3/2003 | Tamura | |
| 2007/0074907 A1* | 4/2007 | Weekamp | G01R 33/09 174/521 |
| 2007/0080682 A1 | 4/2007 | Govari et al. | |
| 2014/0261456 A1* | 9/2014 | Malackowski | A61B 46/10 128/849 |
| 2014/0276004 A1 | 9/2014 | Strupeck et al. | |
| 2016/0135668 A1 | 5/2016 | Gat et al. | |
| 2017/0059361 A1* | 3/2017 | Nagarkar | A61B 5/062 |
| 2018/0220927 A1 | 8/2018 | Kelly et al. | |
| 2018/0220928 A1 | 8/2018 | Blood et al. | |
| 2018/0220929 A1 | 8/2018 | Blood et al. | |
| 2019/0056242 A1 | 2/2019 | Foster et al. | |
| 2019/0217059 A1 | 7/2019 | Meyer et al. | |
| 2020/0188635 A1* | 6/2020 | Barrish | A61B 34/20 |
| 2021/0052191 A1* | 2/2021 | Olson | A61B 5/062 |
| 2022/0001140 A1 | 1/2022 | Meyer et al. | |
| 2022/0265194 A1 | 8/2022 | Govari et al. | |

OTHER PUBLICATIONS

International Search Report and Written Opinion issued in PCT/US2022/029782, mailed Aug. 11, 2022, 11 pages.

* cited by examiner

MAGNETIC FIELD SENSOR FOR A MEDICAL DEVICE

CROSS REFERENCE TO RELATED APPLICATION

This application claims priority to Provisional Application No. 63/190,537, filed May 19, 2021, which is herein incorporated by reference in its entirety.

TECHNICAL FIELD

The present disclosure relates to systems, methods, and devices for tracking items. More specifically, the disclosure relates to systems, methods, and devices for electro-magnetically tracking medical devices used in medical procedures.

BACKGROUND

A variety of systems, methods, and devices can be used to track medical devices. Tracking systems can use generated magnetic fields that are sensed by at least one tracking sensor in the tracked medical device. The generated magnetic fields provide a fixed frame of reference, and the tracking sensor senses the magnetic fields to determine the location and orientation of the sensor in relation to the fixed frame of reference.

SUMMARY

In Example 1, a magnetic field sensor for a medical device, the magnetic sensor assembly comprising a substrate having a plurality of planar sections, wherein adjacent planar sections are joined by a transition section, and wherein the planar sections are arranged such that an inner surface of the magnetic field sensor is concave, and wherein the plurality of planar sections includes a first planar section oriented in a first plane and a second planar section oriented in a second plane orthogonal to the first plane, a first magneto-resistive (MR) sensor mounted to the first planar section and defining a first axis of sensitivity, and a second MR sensor mounted to the second planar section and defining a second axis of sensitivity.

In Example 2, the magnetic field sensor of Example 1, further comprising a third planar section between the first and second planar sections, and wherein one of the transition sections is interposed between the first and third planar sections, and another of the transition sections is interposed between the third and second planar sections.

In Example 3, the magnetic field sensor of Example 2, wherein the one of the transition sections between the first and third planar sections defines an angle therebetween.

In Example 4, the magnetic field sensor of any of Examples 1-3, further comprising a rigid first cap disposed over the first MR sensor, and a rigid second cap disposed over the second MR sensor.

In Example 5, the magnetic field sensor of any of Examples 1-4, wherein the transition sections are relatively flexible.

In Example 6, the magnetic field sensor of either of Examples 4 or 5, wherein the first and second caps are each cap is configured such that the first and second planar sections are relatively rigid.

In Example 7, the magnetic field sensor of any of Examples 4-6, further comprising a rigid third cap over the third planar section.

In Example 8, the magnetic field sensor of Example 7, wherein the first, second and third caps each have an inner face that together define the concave inner surface of the magnetic field sensor.

In Example 9, the magnetic field sensor of any of Examples 1-8, wherein the substrate has a convex outer surface.

In Example 10, the magnetic field sensor of Example 9, further comprising one or more sensor elements on the convex outer surface of the substrate.

In Example 11, a therapeutic/diagnostic assembly of a medical device, the therapeutic/diagnostic assembly comprising, the magnetic field sensor of any of Examples 1-10, a frame, a magnetic field sensor, and an encapsulating material. The frame has a generally convex outer surface, wherein the concave inner surface of the magnetic field sensor is positioned about the convex outer surface of the frame, and the encapsulating material is disposed over the frame and the magnetic field sensor.

In Example 12, the therapeutic/diagnostic assembly of Example 11, further comprising a lumen extending through the component opposite the magnetic field sensor.

In Example 13, the therapeutic/diagnostic assembly of Example 12, further comprising a therapeutic or diagnostic component mounted to the frame.

In Example 14, the therapeutic/diagnostic assembly of Example 13, wherein the therapeutic or diagnostic component is an imaging element.

In Example 15, the therapeutic/diagnostic assembly of any of Examples 12-14, wherein the lumen is defined collectively by a surface of the frame and a surface of the encapsulating material.

In Example 16, a magnetic field sensor for a medical device, the magnetic sensor comprising a substrate, a first magneto-resistive (MR) sensor, and a second MR sensor. The substrate has a plurality of planar sections, wherein adjacent planar sections are joined by a transition section, and wherein the planar sections are arranged in a substantially C-shaped arrangement such that an inner surface of the magnetic field sensor is concave, and wherein the plurality of planar sections includes a first planar section oriented in a first plane and a second planar section oriented in a second plane orthogonal to the first plane. The first MR sensor is mounted to the first planar section and defines a first axis of sensitivity, and the second MR sensor is mounted to the second planar section and defines a second axis of sensitivity.

In Example 17, the magnetic field sensor of Example 16, further comprising a third planar section between the first and second planar sections, and wherein one of the transition sections is interposed between the first and third planar sections, and another of the transition sections is interposed between the third and second planar sections.

In Example 18, the magnetic field sensor of Example 17, wherein the one of the transition sections between the first and third planar sections defines an angle therebetween.

In Example 19, the magnetic field sensor of Example 17, further comprising a rigid first cap disposed over the first MR sensor, and a rigid second cap disposed over the second MR sensor.

In Example 20, the magnetic field sensor of Example 19, wherein the transition sections are relatively flexible.

In Example 21, the magnetic field sensor of Example 20, wherein the first and second caps are each cap is configured such that the first and second planar sections are relatively rigid.

In Example 22, the magnetic field sensor of Example 21, further comprising a rigid third cap over the third planar section.

In Example 23, the magnetic field sensor of Example 22, wherein the first, second and third caps each have an inner face that together define the concave inner surface of the magnetic field sensor.

In Example 24, the magnetic field sensor of Example 16, wherein the substrate has a convex outer surface.

In Example 25, the magnetic field sensor of Example 24, further comprising one or more sensor elements on the convex outer surface of the substrate.

In Example 26, a medical device comprising a handle accessible by a user, a shaft having a proximal portion attached to the handle, and an opposite distal end, and a therapeutic/diagnostic assembly at the distal end of the shaft. The therapeutic/diagnostic assembly comprises a frame, a magnetic field sensor and an encapsulating material. The frame has a generally convex outer surface. The magnetic field sensor is mounted on convex surface of the frame, and comprises a substrate, a first magneto-resistive (MR) sensor and a second MR sensor. The substrate has a plurality of planar sections, wherein adjacent planar sections are joined by a transition section, and wherein the planar sections are arranged such that the magnetic field sensor has a concave inner surface, and wherein adjacent planar sections are joined by a transition section, and wherein the planar sections are arranged such that a first planar section lies in a first plane and a second planar section lies in a second plane orthogonal to the first plane. The first (MR) sensor is mounted to the first planar section and defines a first axis of sensitivity, and the second (MR) sensor is mounted to the second planar section and defines a second axis of sensitivity, wherein the concave inner surface of the magnetic field sensor is positioned about the convex outer surface of the frame. The encapsulating material is disposed over the frame and the magnetic field sensor.

In Example 27, the medical device of Example 26, further comprising a third planar section between the first and second planar sections, and wherein one of the transition sections is interposed between the first and third planar sections, and another of the transition sections is interposed between the third and second planar sections.

In Example 28, the medical device of Example 27, wherein the one of the transition sections between the first and third planar sections defines an angle therebetween.

In Example 29, the medical device of Example 27, further comprising a rigid first cap disposed over the first MR sensor, and a rigid second cap disposed over the second MR sensor.

In Example 30, the medical device of Example 29, wherein the first and second caps are each cap is configured such that the first and second planar sections are relatively rigid.

In Example 31, the medical device of Example 30, further comprising a rigid third cap over the third planar section.

In Example 32, the medical device of Example 31, wherein the first, second and third caps each have an inner face that together define the concave inner surface of the magnetic field sensor.

In Example 33, a method of making a functional assembly for a medical device. The method comprises forming a rigid frame having a generally convex outer surface, mounting a magnetic field sensor to the frame, and forming a rigid encapsulating material over the frame and the magnetic field sensor. The magnetic field sensor has a substrate and first and second MR sensors mounted to the substrate and arranged such that the first MR sensor has an axis of sensitivity that is orthogonal to an axis of sensitivity of the second MR sensor, and further wherein the substrate is configured such that the magnetic field sensor is generally C-shaped with a concave inner surface, and wherein mounting the magnetic field sensor to the frame includes positioning the concave inner surface of the magnetic field sensor over the concave outer surface of the frame.

In Example 34, the method of Example 33, wherein the magnetic field sensor has a plurality of planar sections including a first planar section and a second planar section, and wherein the first MR sensor is mounted to the first planar section and the second MR sensor is mounted to the second planar section.

In Example 35, the method of Example 34, wherein the magnetic field sensor further comprises a third planar section between the first and second planar sections.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
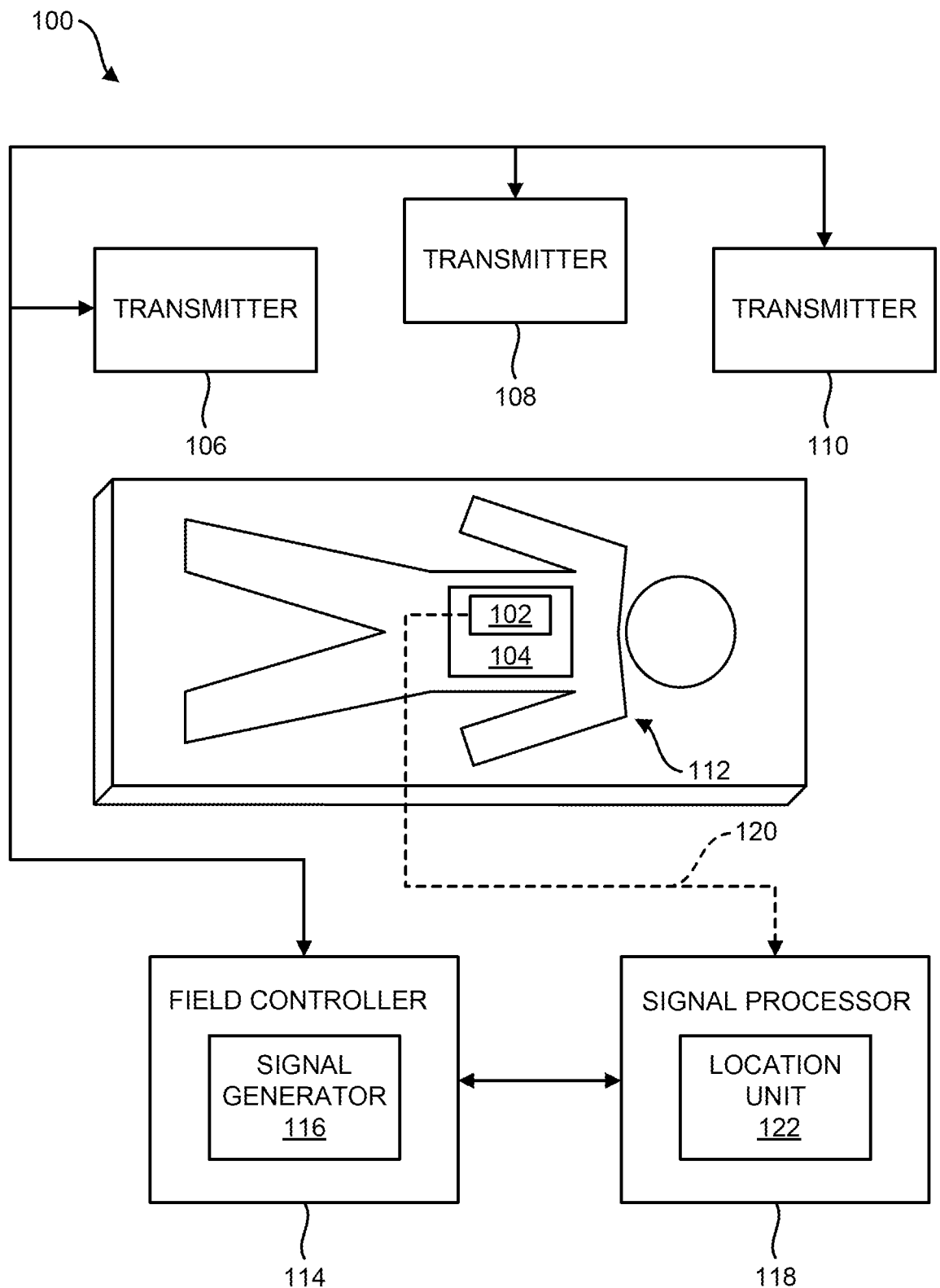
FIG. 1 shows a schematic of a tracking system, in accordance with certain embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

During medical procedures, medical devices such as probes (e.g., catheters, guidewires, scopes) are inserted into a patient. To track the location and orientation of a probe within the patient, probes can be provisioned with magnetic field sensors that detect various magnetic fields generated by transmitters near the patient.

FIG. 1 is a schematic block diagram depicting a tracking system 100 that is configured to determine location information corresponding to the medical device 104 based on information collected using a receiver (e.g., sensor) 102 associated with a medical device 104. The information collected by the receiver 102 includes a received field signal corresponding to an electromagnetic field defined by a set of electromagnetic signals transmitted by one or more magnetic field transmitter assemblies 106, 108, and 110. According to embodiments, one or more magnetic field transmitter assemblies 106, 108, and 110, are configured to transmit (e.g., radiate) electromagnetic signals, which produce a magnetic field within which a subject 112 is disposed. According to embodiments, the system 100 includes a magnetic field controller 114 configured to manage operation of the magnetic field transmitter assemblies 106, 108, and 110.

The receiver 102 (e.g., magnetic field sensor) (which may include one or more receivers/sensors) may be configured to produce an electrical response to the magnetic field(s) generated by the magnetic field transmitter assemblies 106, 108, and 110. For example, the receiver 102 may include one or more magnetic field sensors such as inductive sensing coils and/or various sensing elements such as magnetoresistive (MR) sensing elements (e.g., anisotropic magnetoresistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or flux-gate sensing elements. The receiver 102 is configured to sense the generated magnetic fields and provide tracking signals indicating the location and orientation of the receiver 102 in up to six degrees of freedom (i.e., x, y, and z measurements, and pitch, yaw, and roll angles). Generally, the number of degrees of freedom that a tracking system is able to track depends on the number of magnetic field sensors and magnetic field generators. For example, a tracking system with a single magnetic field sensor may not be capable of tracking roll angles and thus are limited to tracking in only five degrees of freedom (i.e., x, y, and z coordinates, and pitch and yaw angles). This is because a magnetic field sensed by a single magnetic field sensor does not change as the single magnetic field sensor is "rolled." The magnetic field sensors can be powered by voltages or currents to drive or excite elements of the magnetic field sensors. The magnetic field sensor elements receive the voltage or current and, in response to one or more of the generated magnetic fields, the magnetic field sensor elements generate sensing signals, which are transmitted to the magnetic field controller 114.

As shown in FIG. 1, the magnetic field controller 114 includes a signal generator 116 configured to provide driving current to each of the magnetic field transmitter assemblies 106, 108, and 110, causing each magnetic field transmitter assembly to transmit an electromagnetic signal. In certain embodiments, the signal generator 116 is configured to provide variable (e.g., sinusoidal) driving currents to the magnetic field transmitter assemblies 106, 108, and 110. The magnetic field controller 114 can be implemented using firmware, integrated circuits, and/or software modules that interact with each other or are combined together. For example, the magnetic field controller 114 may include computer-readable instructions/code for execution by a processor (see FIG. 2). Such instructions may be stored on a non-transitory computer-readable medium (see FIG. 2) and transferred to the processor for execution. In some embodiments, the magnetic field controller 114 can be implemented in one or more application-specific integrated circuits and/or other forms of circuitry suitable for controlling and processing magnetic tracking signals and information.

The sensed magnetic field signal may include multiple magnetic field signals, each of which may be processed to extract field components corresponding to one or more magnetic field transmitter assemblies. The sensed magnetic field signal is communicated to a signal processor 118, which is configured to analyze the sensed magnetic field signal to determine location information corresponding to the receiver 102 (and, thus, the medical device 104). Location information may include any type of information associated with a location and/or position of a medical device 104 such as, for example, location, relative location (e.g., location relative to another device and/or location), position, orientation, velocity, acceleration, and/or the like. As mentioned above, rotating magnetic field-based tracking can utilize phase (e.g., differences in phase) of the sensed magnetic field signal to determine location and orientation of the probe.

The tracking system 100 can also include at least one sensor that is configured and arranged to sense the magnetic fields generated by the magnetic field transmitter assemblies, 106-110. The sensor can be a magnetic sensor (e.g., dual-axis magnetic sensor, tri-axis magnetic sensor) and be positioned at a known reference point in proximity to the magnetic field transmitter assemblies, 106-110, to act as a reference sensor. For example, one or more sensors can be coupled to the subject's bed, the subject herself, an arm of an x-ray machine, or at other points a known distance from the magnetic field transmitter assemblies, 106-110. In some embodiments, the at least one sensor is mounted to one of the magnetic field transmitter assemblies, 106-110.

The medical device 104 may include, for example, an endoscope, an endoscopic probe or cannula, a catheter (e.g., a mapping catheter, an ablation catheter, a diagnostic catheter, an introducer), an implantable medical device (e.g., a control device, a monitoring device, a pacemaker, an implantable cardioverter defibrillator (ICD), a cardiac resynchronization therapy (CRT) device, a CRT-D), guidewire, biopsy needle, ultrasound device, reference patch, robot and/or the like. For example, in embodiments, the medical device 104 may be an imaging endoscopic probe. In other embodiments, the medical device 104 may include a mapping catheter associated with an anatomical mapping system. In still other embodiments, the medical device 104 may be an ablation catheter. The medical device 104 may include any other type of device configured to be at least temporarily disposed within a subject 112. The subject 112 may be a human, a dog, a pig, and/or any other animal having physiological parameters that can be recorded. For example, in embodiments, the subject 112 may be a human patient.

As shown in FIG. 1, the medical device 104 may be configured to be disposed within the body of a subject 112 and may be configured to be communicatively coupled to the signal processor 118 via a communication link 120 (shown in phantom). In embodiments, the communication link 120 may be, or include, a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two devices, and should not be understood to be limited to a direct, persistent, or otherwise limited communication channel. That is, in some embodiments, the communication link 120 may be a persistent communication link, an intermittent communication link, an ad-hoc communication link, and/or the like. The communication link 120 may refer to direct communications between the medical device 104 and the signal processor 118, and/or indirect communications that travel between the medical device 104 and the signal processor 118 via at least one other device (e.g., a repeater, router, hub, and/or the like). The communication link 120 may facilitate uni-directional and/or bi-directional communication between the medical device 104 and the signal processor 118. Data and/or control signals may be transmitted between the medical device 104 and the signal processor 118 to coordinate the functions of the medical device 104 and/or the signal processor 118.

The signal processor 118 further includes a location unit 122 configured to determine, based on the sensed field signal (e.g., the phase, amplitude, differences in phase and/or amplitude of the sensed field signal), location information corresponding to the medical device 104. The location unit 122 may be configured to determine location information according to any location-determination technique that uses magnetic navigation. According to various embodiments of the disclosed subject matter, any number of the components depicted in FIG. 1 (e.g., the field controller 114, the signal generator 116, the signal processor 118) may be implemented on one or more computing devices, either as a single unit or a combination of multiple devices. The system 100 can include a display for visualizing the position and/or orientation of the medical device 104 in the subject 112.

Figure 2:
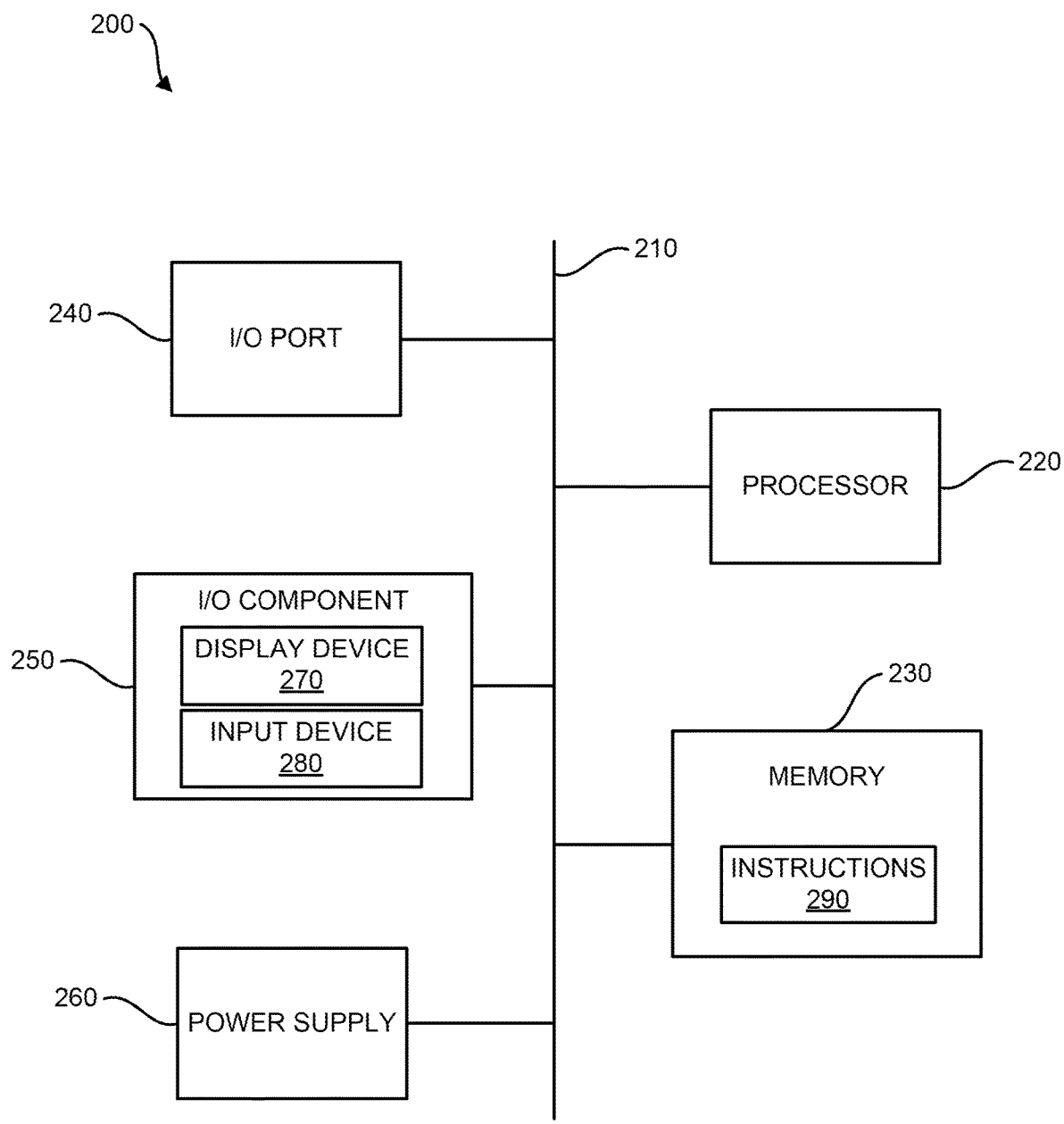
FIG. 2 shows a block representation of a computing device, in accordance with certain embodiments of the present disclosure.

FIG. 2 is a schematic block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "general-purpose graphics processing units (GPGPUs)," and the like, all of which are contemplated within the scope of FIGS. 1 and 2, with reference to various components of the tracking system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices. As an example only, the processor 220 may include the signal processor 118, but other suitable configurations are also contemplated to suit different applications.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 290 for causing the processor 220 to implement aspects of embodiments of system components discussed herein and/or to perform aspects of embodiments of methods and procedures discussed herein.

The computer-executable instructions 290 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
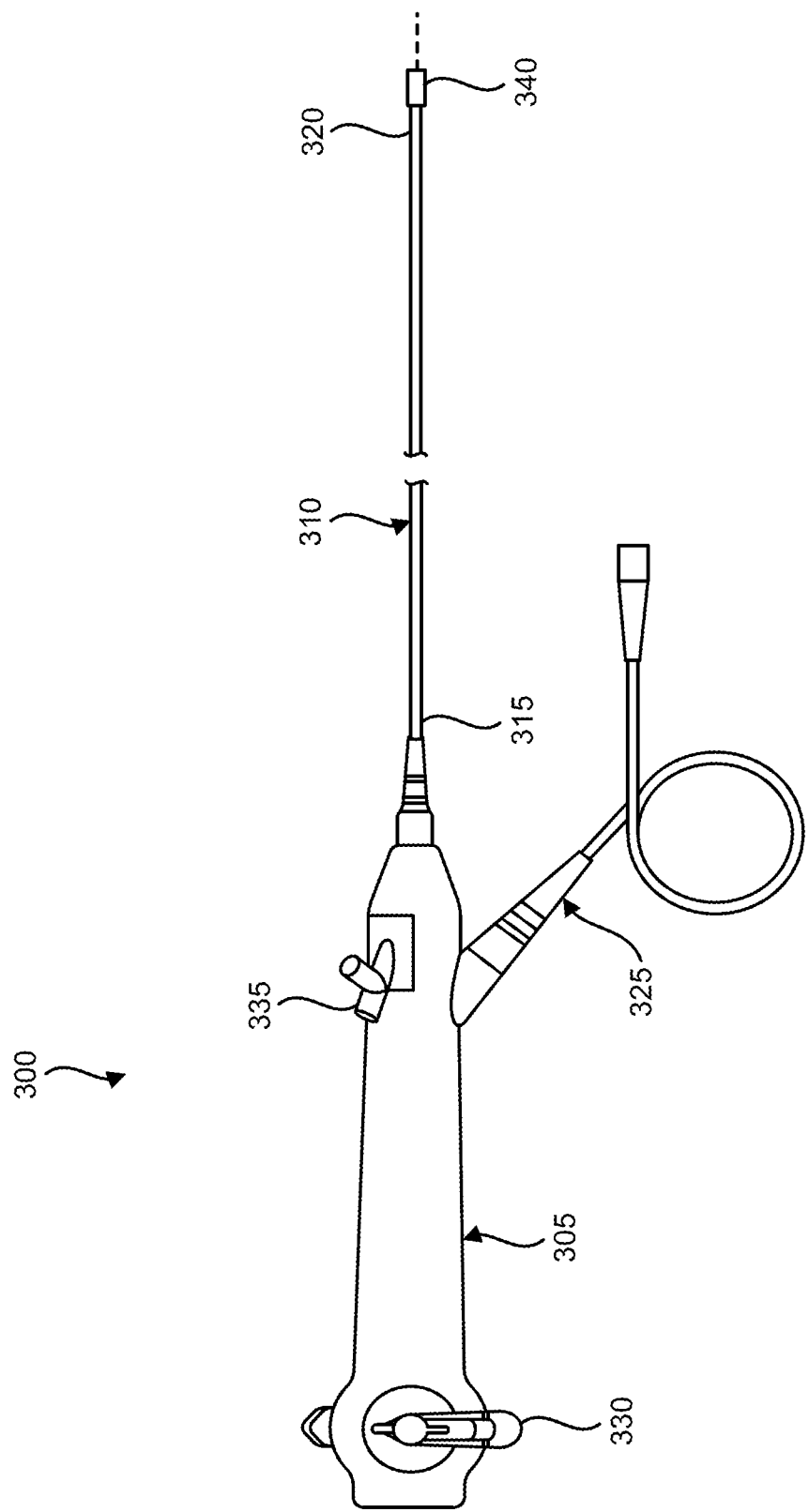
FIG. 3 is an illustration of a portion of an exemplary medical device, in accordance with certain embodiments of the present disclosure.

FIG. 3 is an illustration of a portion of an exemplary medical device 300, in accordance with certain embodiments of the present disclosure. In the particular example shown, the medical device 300 is an endoscopic probe, although as discussed above, in other embodiments the medical device 300 could be any number of devices for which the user can benefit from the capability to track and visualize the device within the patient's body. As shown in FIG. 3, the medical device 300 includes a handle 305, a shaft 310 having a proximal end portion 315 extending distally from the handle 305, and an opposite distal end portion 320. In the illustrated embodiment, as is typical of an endoscopic probe/device, the medical device 300 further includes a flush port assembly 325, a deflection actuator 330, and an access port 335 all located in or on the handle 305 to facilitate the functional operation of the medical device 300.

As further shown, the distal end portion 320 includes a therapeutic/diagnostic assembly 340 configured for use in performing the particular therapeutic and/or diagnostic procedures within the patient's body. As will be discussed in greater detail herein, the therapeutic/diagnostic assembly 340 includes a flexible circuit-based magnetic field sensor for enabling magnetic tracking and localization of the therapeutic/diagnostic assembly 340 within the body as described in connection with FIGS. 1 & 2. Furthermore, as will be shown and explained in detail below, the magnetic field sensor of the present disclosure has a novel form factor that minimizes space requirements while still providing for 5 or 6 degree-of-freedom magnetic tracking. Small diameter medical devices, such as those described above, have minimal space available for components not directly related to their therapeutic and/or diagnostic functions. The novel magnetic field sensor of the present disclosure remedies this problem by providing a form factor that allows it to be integrated into the outer-most diameter portion of the device shaft.

Figure 4:
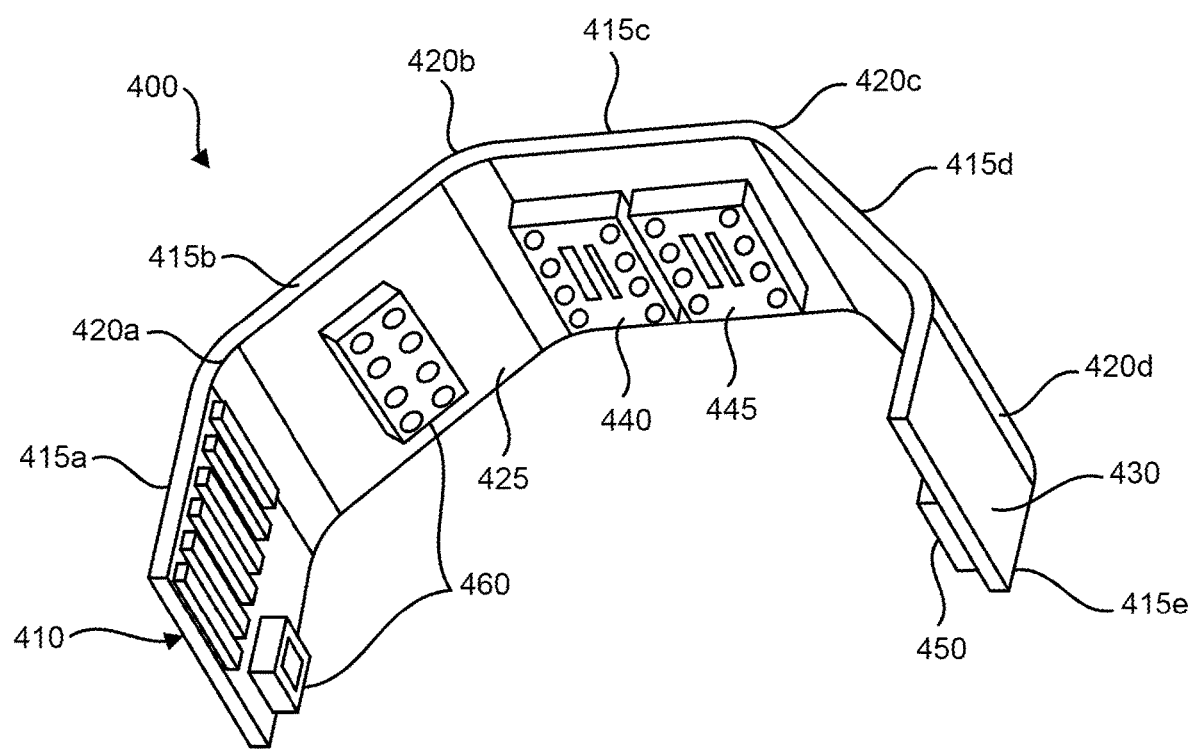
FIG. 4 is a perspective view of an exemplary magnetic field sensor for use in the medical device of FIG. 3, in accordance with certain embodiments of the present disclosure.

With the foregoing in mind, FIG. 4 is a perspective view of an exemplary magnetic field sensor 400 for use in therapeutic/diagnostic assembly 340 discussed above. As shown, the overall shape of the magnetic field sensor 400 is generally C-shaped, with a concave inner surface 425 and a convex outer surface 430. As such, the shape of the magnetic field sensor 400 is complementary to the generally cylindrical shape of the medical device shaft 305, such that it can be integrated into the therapeutic/diagnostic assembly 340 while still maximizing space in the interior of the shaft 305 for other necessary components.

In the illustrated embodiment, the magnetic field sensor 400 includes a flexible circuit substrate 410 that includes a plurality of planar sections 415a, 415b, 415c, 415d and 415e. As further shown, the substrate 410 includes a transition section 420a between the planar sections 415a and 415b, a transition section 420b between planar sections 415b and 415c, a transition section 420c between planar sections 415c and 415d, and a transition section 420d between planar sections 415d and 415e. As can be seen in FIG. 4, the transition sections 420a, 420b, 420c and 420d are arranged so that the planar sections that they lie between are oriented at an angle relative to one another, so that the overall shape of the substrate 410, and accordingly, the magnetic field sensor 400, is generally C-shaped.

As further shown, the magnetic field sensor 400 includes a plurality of magnetic field sensing elements, which in the illustrated embodiment are represented by magnetoresistive (MR) sensors 440, 445, 450. In the exemplary embodiment illustrated, additional electronic components 460, e.g., filters and the like, as well as connection pads for terminating conductor wires, can be included on the substrate 410. Additionally, as will be appreciated, the substrate 410 includes other elements typical of flex circuits, e.g., electrical traces to allow for electrical connectivity between the respective MR sensors 440, 445, 450 and processing equipment. Such additional components and flex circuit features are well known in the art and are not critical to the present disclosure, and thus will not be further discussed herein.

As shown, the MR sensors 440, 445 are positioned on the planar section 415c and the MR sensor 450 is positioned on the planar section 415e. Further, the planar sections are arranged such that the planar section 415c is oriented orthogonal to the planar section 415e so as to define two mutually orthogonal primary sensing axes on which the respective MR sensors are positioned. As will be appreciated, in the particular embodiment shown, the MR sensors 440, 445 may be oriented such that their respective primary sensing axes are 90 degrees apart. In this manner the overall MR sensor arrangement provides for three mutually orthogonal primary sensing axes.

It is emphasized, however, that the particular arrangement shown in FIG. 4 is exemplary only, and other arrangements of the various components can be employed within the scope of the present disclosure. For example, the magnetic field sensor 400 may include fewer or more than three MR sensors, or fewer or more than five planar sections. Furthermore, the specific planar section on which any particular MR sensor is positioned is not critical. Additionally, the planar sections on which the MR sensors 440 (or 445) and 450 are positioned need not be orthogonal to one another so long as the relative angle therebetween is known.

Figure 5A:
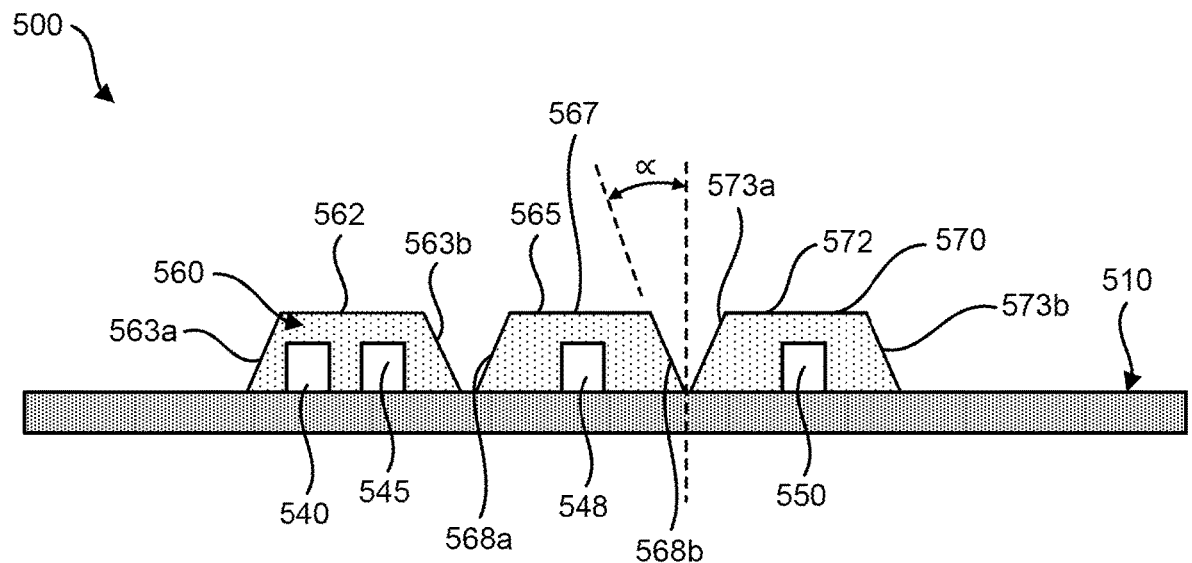
FIGS. 5A-5B are schematic illustrations of an end view of a magnetic field sensor, in accordance with certain embodiments of the present disclosure.
Figure 5B:
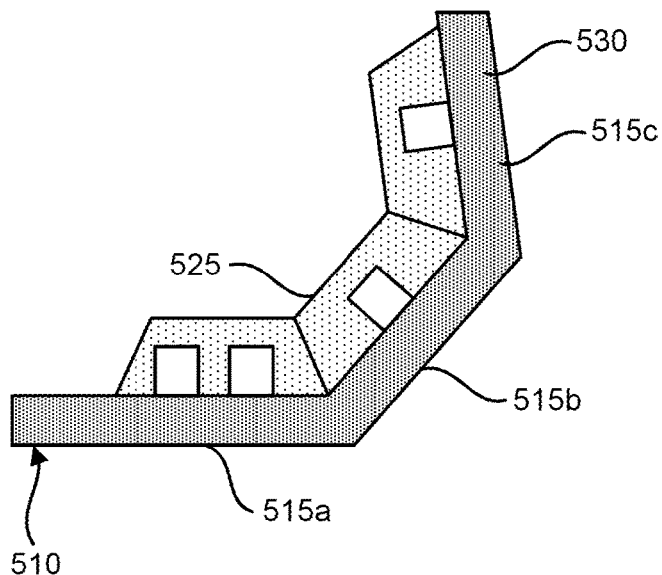

FIGS. 5A&5B are end views of an exemplary magnetic field sensor 500 (which could correspond to a portion of the magnetic field sensor 400) illustrating how the C-shaped profile can be formed, with FIG. 5A illustrating the magnetic field sensor 500 prior to forming the C-shaped profile. As shown, the magnetic field sensor 500 includes a substrate 510, planar sections 515a, 515b, 515c (FIG. 5B), an inner surface 525 and an outer surface 530. As further shown, the magnetic field sensor 500 includes, for example, MR sensors 540, 545, 548 and 550. In the illustrated embodiment, the MR sensors 540 and 545 are located on the planar section 515a, the MR sensor 548 is located on the planar section 515b and the MR sensor 550 is located on the planar section 515c. As further shown, a cap 560 having an inner face 562 and opposing side faces 563a, 563b overlies the MR sensors 540, 545, a cap 565 having an inner face 567 and opposing side faces 568a, 568b overlies the MR sensor 548, and a cap 570 having an inner face 572 and opposing side faces 573a, 573b overlies the MR sensor 550. The caps 560, 565 and 570 can be formed from a relatively hard dielectric material (e.g., a molded epoxy as is known in the art) and enhance the rigidity of the respective planar sections while at the same time form protective covers over the respective MR sensors.

Additionally, as can be seen in FIG. 5A, the side faces 563a, 563b are angled, as are the side faces 568a, 568b and 573a, 573b. Furthermore, the adjacent side faces 563b and 568a are oriented at divergent angles relative to one another, as are the adjacent side faces 568b and 573a. In this way, the junction between the respective adjacent side faces forms the corresponding transition section (refer to FIG. 4), thus allowing the flexible substrate 510 to be bent to form the corresponding planar sections. Additionally, the side faces, e.g., the side faces 568b and 573a as shown, define the bend angle α and thus the angle between the planar sections 515b, 515c, and also act to delimit the degree of bending therebetween as they abut one another. By tailoring the particular geometry of the side angles, the overall geometry of the magnetic field sensor 500 when formed. Additionally, as can be seen in FIG. 5B, the inner faces 562, 567 and 572 collectively form the inner surface 525 of the magnetic field sensor 500.

In the various embodiments, the magnetic field sensors 400, 400 described herein can be formed of materials and manufactured according to known techniques for forming flexible circuits, modified as discussed herein. Although in the illustrated embodiments the MR sensors are disposed on the inner surfaces of the substrate, this is not critical, and thus in various embodiments, one or more of the MR sensors could be disposed on the outer surface of the substrate. Additionally, although the exemplary embodiments are described as utilizing MR sensors, other types of magnetic field sensors (as listed above herein) could be utilized within the scope of the present disclosure.

Furthermore, in embodiments, additional components not directly related to magnetic field sensing could be integrated into the magnetic field sensors 400, 500. For example, in embodiments the structure of the magnetic field sensors 400, 500 can facilitate the inclusion of other types of sensors. In one particular example, one or more electrodes could be positioned or formed on the outer surface of the substrate, which could be utilized, for example, to sense intrinsic cardiac signals for use in cardiac electrophysiology procedures. Still additionally, other types of sensors, e.g., ultrasound transducers, pressure sensors, temperature sensors, and the like, could be incorporated into the outer surface of the substrate.

Figure 6A:
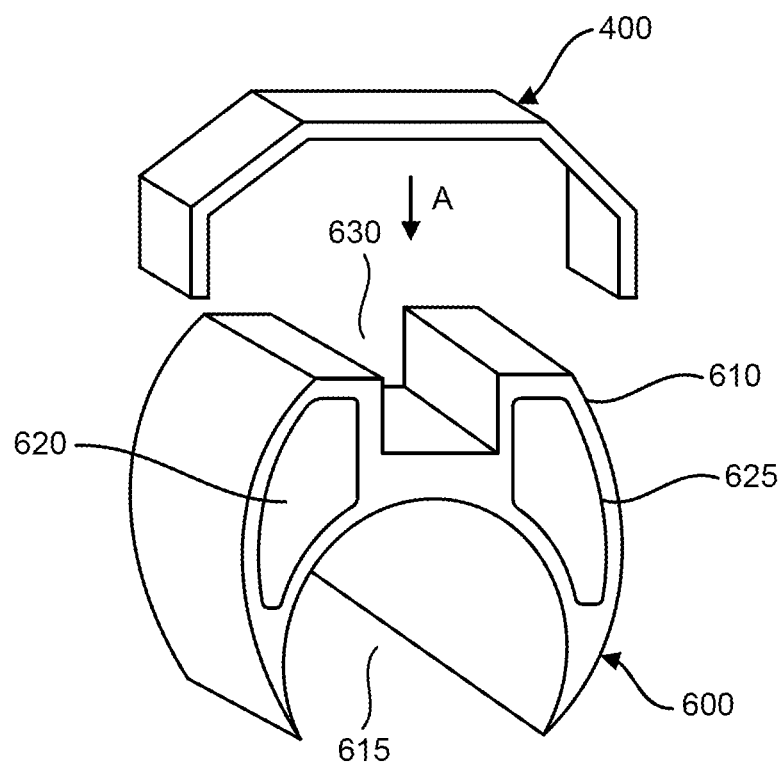
FIGS. 6A-6B are perspective illustrations of portions of a therapeutic/diagnostic assembly of the medical device of FIG. 3, in accordance with certain embodiments of the disclosure.
Figure 6B:
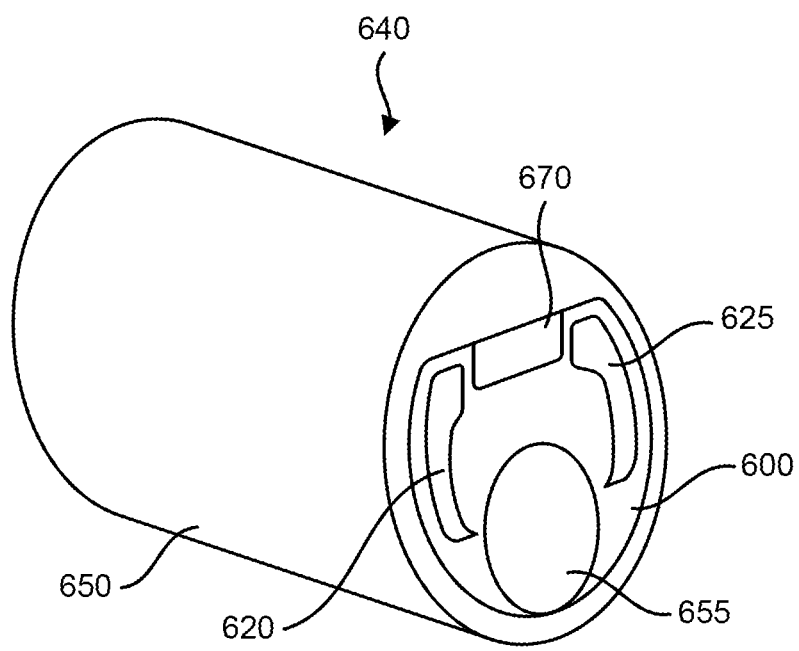

FIGS. 6A-6B illustrate an example of the integration of the magnetic field sensor 400 into therapeutic/diagnostic assembly for a medical device application, in this case, an imaging endoscope cap. FIG. 6A is a perspective view of a portion of an endoscope cap in an intermediate stage of manufacture. As shown, a frame 600 can be formed, e.g., using a low-pressure epoxy potting or comparable method as is known in the art. The illustrated frame 600 has a partially cylindrical shape defining a generally convex outer surface profile 610. In the particular example, a lower portion 615 of the frame 600 forms a semi-circular recess which can correspond to a lumen in the finished scope cap (FIG. 6B). As further shown, illumination elements 620, 625 are positioned within the frame 600, and a recess 630 opposite the lower portion 615 is formed to accommodate an imaging element as is known in the art.

As can be seen in FIG. 6A, the overall convex shape of the outer surface 610 of the frame 600 is complementary to the generally concave inner surface of the magnetic field sensor 400. As such, the magnetic field sensor 400 can be mounted over the frame 600. In embodiments, the frame 600 may also include a recess to receive the magnetic field sensor to further minimize the overall diameter of the assembly. The magnetic field sensor 400 can be mounted in a pre-formed configuration (as shown) or alternatively can be form-fit from its flat configuration (similar to that shown in FIG. 5A for the magnetic field sensor 500) once placed on the frame 600.

FIG. 6B illustrates the completed scope cap 640, which includes a second, encapsulating material 650 over the frame 600 and the magnetic field sensor 400 (not visible in FIG. 6B). The encapsulating material 650 can be formed in a secondary potting process from the same material as the frame 600, or by using another material or suitable manufacturing process. As further shown in FIG. 6B, in the completed scope cap 640, a major lumen 655 is formed by the combination of the frame 600 and the encapsulating material for use in introducing secondary components, e.g., resecting instruments and the like. Additionally, the imaging element 670 is positioned in the recess 630 of the frame 600 (FIG. 6A). The overall construction of the scope cap 640 as described herein thus provides the capability of magnetically tracking the position of the scope cap 640 in the body in six degrees-of-freedom while maximizing the size of the lumen 655. As discussed elsewhere herein, the particular scope cap application described and shown in FIGS. 6A-6B is just one exemplary embodiment of an application of the novel magnetic field sensors of the present disclosure.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A magnetic field sensor for a medical device, the magnetic field sensor comprising:
    a substrate having a plurality of planar sections, wherein adjacent planar sections are joined by a transition section, and wherein the planar sections are arranged in a substantially C-shaped arrangement such that an inner surface of the magnetic field sensor is concave, and wherein the plurality of planar sections includes a first planar section oriented in a first plane and a second planar section oriented in a second plane orthogonal to the first plane, and a third planar section oriented in a third plane, the third planar section adjacent the first planar section, wherein the C-shaped arrangement is complementary to a cylindrical shape of a medical device shaft such that the C-shaped arrangement can be integrated into an outer-most diameter portion of the medical device shaft;
    a first magneto-resistive (MR) sensor mounted to the first planar section and defining a first primary sensing axis;
    a second MR sensor mounted to the second planar section and defining a second primary sensing axis; and
    wherein the inner surface is defined by a plurality of rigid caps disposed on the substrate, the plurality of rigid caps including a rigid first cap disposed over the first MR sensor, a rigid second cap disposed over the second MR sensor, and a rigid third cap over the third planar section.

2. The magnetic field sensor of claim 1, wherein the third planar section is positioned between the first and second planar sections, and wherein one of the transition sections is interposed between the first and third planar sections, and another of the transition sections is interposed between the third and second planar sections.

3. The magnetic field sensor of claim 2, wherein the one of the transition sections between the first and third planar sections defines an angle therebetween.

4. The magnetic field sensor of claim 1, wherein the transition sections are flexible.

5. The magnetic field sensor of claim 4, wherein the first and second rigid caps are configured such that the first and second planar sections are rigid.

6. The magnetic field sensor of claim 5, wherein the first, second and third caps each have an inner face that together define the concave inner surface of the magnetic field sensor.

7. The magnetic field sensor of claim 1, wherein the substrate has a convex outer surface.

8. The magnetic field sensor of claim 7, further comprising one or more sensor elements on the convex outer surface of the substrate.

9. A medical device comprising:
    a handle accessible by a user;
    a shaft having a proximal portion attached to the handle, and an opposite distal end;
    a therapeutic or diagnostic assembly at the distal end of the shaft, the therapeutic/diagnostic assembly comprising:
    a medical device cap having a generally convex outer surface;
    a magnetic field sensor mounted on the convex outer surface of the medical device cap, wherein the magnetic field sensor comprises:
    a substrate having a plurality of planar sections, wherein adjacent planar sections are joined by a transition section, and wherein the planar sections are arranged such that the magnetic field sensor has a concave inner surface, and wherein the planar sections are arranged such that a first planar section lies in a first plane and a second planar section lies in a second plane orthogonal to the first plane, and a third planar section oriented in a third plane, the third planar section adjacent the first planar section;

a first magneto-resistive (MR) sensor mounted to the first planar section and defining a first primary sensing axis; and a second (MR) sensor mounted to the second planar section and defining a second primary sensing axis, wherein the inner surface is defined by a plurality of rigid caps disposed on the substrate, the plurality of rigid caps including a rigid first cap disposed over the first MR sensor, a rigid second cap disposed over the second MR sensor, and a rigid third cap over the third planar section, wherein the rigid first cap, the rigid second cap, and the rigid third cap include an inner face and side faces, the side faces being oriented at divergent angles relative to one another to delimit bending therebetween as the rigid caps abut one another; and an encapsulating material disposed over the medical device cap and the magnetic field sensor.

10. The medical device of claim 9, wherein the third planar section is disposed between the first and second planar sections, and wherein one of the transition sections is interposed between the first and third planar sections, and another of the transition sections is interposed between the third and second planar sections.

11. The medical device of claim 10, wherein the one of the transition sections between the first and third planar sections defines an angle therebetween.

12. The medical device of claim 9, wherein the first and second rigid caps are configured such that the first and second planar sections are rigid.

13. The medical device of claim 9, wherein the first, second and third caps each have an inner face that together define the concave inner surface of the magnetic field sensor.

14. A method of making a functional assembly for a medical device, the method comprising:

forming a rigid frame of a medical device having a generally convex outer surface and a lower portion including a semi-circular recess;

mounting a magnetic field sensor to the frame, wherein the magnetic field sensor has a substrate and first and second magneto-resistive (MR) sensors mounted to the substrate and arranged such that the first MR sensor has an axis of sensitivity that is orthogonal to an axis of sensitivity of the second MR sensor, and further wherein the substrate is configured such that the magnetic field sensor is generally C-shaped with a concave inner surface, and wherein mounting the magnetic field sensor to the frame of the medical device includes positioning the concave inner surface of the magnetic field sensor over the convex outer surface of the frame;

the substrate having a plurality of planar sections, wherein adjacent planar sections are joined by a transition section, and wherein the planar sections are arranged such that the magnetic field sensor has a concave inner surface, and wherein the planar sections are arranged such that a first planar section lies in a first plane and a second planar section lies in a second plane orthogonal to the first plane, and a third planar section oriented in a third plane, the third planar section adjacent the first planar section; and forming a rigid encapsulating material over the frame and the magnetic field sensor, the rigid encapsulating material including a rigid first cap disposed over the first MR sensor, a rigid second cap disposed over the second MR sensor, and a rigid third cap over the third planar section.

15. The method of claim 14, wherein the magnetic field sensor has a plurality of planar sections including a first planar section and a second planar section, and wherein the first MR sensor is mounted to the first planar section, the second MR sensor is mounted to the second planar section, and the third planar section is positioned between the first and second planar sections, and wherein one of the transition sections is interposed between the first and third planar sections, and another of the transition sections is interposed between the third and second planar sections.

16. The method of claim 15, wherein the one of the transition sections between the first and third planar sections defines an angle therebetween.

* * * * *